United States Patent
DiFoggio

(10) Patent No.: US 7,576,856 B2
(45) Date of Patent: Aug. 18, 2009

(54) METHOD AND APPARATUS FOR ESTIMATING A PROPERTY OF A FLUID DOWNHOLE

(75) Inventor: Rocco DiFoggio, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 336 days.

(21) Appl. No.: 11/330,283

(22) Filed: Jan. 11, 2006

(65) Prior Publication Data

US 2007/0159625 A1    Jul. 12, 2007

(51) Int. Cl.
G01J 3/18 (2006.01)
G01J 3/42 (2006.01)

(52) U.S. Cl. .................. 356/328; 250/269.1

(58) Field of Classification Search .............. 356/328, 356/334; 250/256, 269.1
See application file for complete search history.

(56) References Cited

U.S. PATENT DOCUMENTS

| | | | |
|---|---|---|---|
| 5,757,536 A * | 5/1998 | Ricco et al. ............... 359/224 |
| 5,905,571 A | 5/1999 | Butler et al. | |
| 6,437,326 B1 * | 8/2002 | Yamate et al. ........... 250/269.1 |
| 2001/0030745 A1 | 10/2001 | He et al. | |
| 2001/0030746 A1 | 10/2001 | Hamm et al. | |
| 2002/0030814 A1 | 3/2002 | Mikes et al. | |
| 2002/0048066 A1 | 4/2002 | Antoniades et al. | |
| 2002/0070198 A1 | 6/2002 | Brusasco et al. | |
| 2002/0105725 A1 | 8/2002 | Sweatt et al. | |
| 2002/0132316 A1 | 9/2002 | Wang et al. | |
| 2002/0167245 A1 | 11/2002 | Hung et al. | |
| 2002/0167695 A1 | 11/2002 | Senturia | |
| 2002/0191913 A1 | 12/2002 | Hocker et al. | |
| 2003/0039008 A1 | 2/2003 | Davies | |
| 2003/0047665 A1 | 3/2003 | Livermore | |
| 2003/0067601 A1 | 4/2003 | Asami et al. | |
| 2003/0072068 A1 | 4/2003 | Deutsch et al. | |
| 2003/0128419 A1 | 7/2003 | Alaruri et al. | |
| 2003/0179373 A1 | 9/2003 | Magnusson et al. | |
| 2003/0231308 A1 | 12/2003 | Granger | |
| 2003/0231889 A1 | 12/2003 | Brown et al. | |
| 2004/0008523 A1 | 1/2004 | Butler | |
| 2004/0145737 A1 | 7/2004 | Hocker | |
| 2004/0145738 A1 | 7/2004 | Sun et al. | |
| 2004/0160603 A1 | 8/2004 | Reel | |
| 2004/0239930 A1 | 12/2004 | Sakai | |

(Continued)

FOREIGN PATENT DOCUMENTS

WO    WO 2004/023174 A2    3/2004

OTHER PUBLICATIONS

Alan G. Marshall & Ryan P. Rodgers, Petroleomics: The Next Grand Challenge for Chemical Analysis, Acc. chem. Res., 37 (1), 53-59, 2004.

(Continued)

*Primary Examiner*—F. L Evans
(74) *Attorney, Agent, or Firm*—G. Michael Roebuck

(57) ABSTRACT

A method and apparatus are provided for determining a property of a fluid downhole by using a tunable optical grating to collect a fluid's spectrum over a wavelength region of interest. A property of the fluid is estimated from spectra that are obtained from light that has interacted with the fluid and then been reflected off of the tunable optical grating onto a photodetector.

25 Claims, 6 Drawing Sheets

U.S. PATENT DOCUMENTS

| | | |
|---|---|---|
| 2005/0002677 A1 | 1/2005 | McAllister et al. |
| 2005/0041247 A1 | 2/2005 | Lerner et al. |
| 2005/0052647 A1 | 3/2005 | Lerner |
| 2005/0057750 A1 | 3/2005 | Schenk et al. |
| 2005/0057751 A1 | 3/2005 | Schenk et al. |
| 2005/0068526 A1 | 3/2005 | Avrutsky |
| 2005/0073680 A1 | 4/2005 | Chrisp et al. |
| 2005/0083523 A1 | 4/2005 | Senturia |
| 2005/0088649 A1 | 4/2005 | Katsunuma |
| 2005/0088657 A1 | 4/2005 | Sugawara et al. |
| 2005/0099618 A1 | 5/2005 | DiFoggio et al. |
| 2005/0179895 A1 | 8/2005 | Puppels |
| 2005/0248760 A1 | 11/2005 | Lerner |
| 2005/0259253 A1 | 11/2005 | Lerner |
| 2005/0264807 A1 | 12/2005 | Lerner |
| 2005/0270527 A1 | 12/2005 | Reel |
| 2006/0023212 A1 | 2/2006 | Nishii et al. |
| 2006/0033913 A1 | 2/2006 | Sato et al. |
| 2006/0038994 A1 | 2/2006 | Chrisp et al. |
| 2006/0038995 A1 | 2/2006 | Chrisp et al. |
| 2006/0050271 A1 | 3/2006 | McDonald |
| 2006/0093362 A1 | 5/2006 | Welch et al. |
| 2006/0103841 A1 | 5/2006 | Ohishi et al. |
| 2006/0132768 A1 | 6/2006 | Chuang et al. |
| 2006/0140529 A1 | 6/2006 | Childers |

OTHER PUBLICATIONS

Mouli Ramani, Considering reconfigurable optical systems, http://www.electronicproducts.com, Electronic Products, Jun. 2004.

http://www.smalltimes.com/document_display.cfm?document_id=8879&keyword=Polychromix&summary=1&startsum=1, Polychromix Unveils Mems-based Spectrometer, Mar. 1, 2005.

http://www.labtechnologist.com/news/ng.asp?id=58404, Jan. 3, 2005.

http://www.polychromix.com/details_spectroscopy_bluebox.php?ID=1, undated.

International Search Report and Written Opinion mailed Oct. 27, 2008.

* cited by examiner

METHOD AND APPARATUS FOR ESTIMATING A PROPERTY OF A FLUID DOWNHOLE

BACKGROUND OF THE INVENTION

1. Field of the Invention

The present invention relates to the field of downhole fluid analysis in hydrocarbon producing wells for determining fluid density, viscosity, and other parameters for a fluid downhole in a borehole during production, monitoring while drilling or wire line operations.

2. Background Information

Oil and gas companies spend large sums of money to find hydrocarbon deposits. Oil companies drill exploration wells in their most promising prospects and use these exploration wells, not only to determine whether hydrocarbons are present but also to determine the properties of those hydrocarbons, which are present.

To determine hydrocarbon properties, oil and gas companies often withdraw some hydrocarbons from the well. Wireline formation testers can be lowered into the well for this purpose. Initially, fluids that are withdrawn may be highly contaminated with filtrates of the fluids ("muds") that were used during drilling. To obtain samples that are sufficiently clean (usually <10% contamination) so that the sample will provide meaningful lab data concerning the formation, formation fluids are generally pumped from the wellbore for 30-90 minutes, while clean up is being monitored in real time. Then, these withdrawn fluids can be collected downhole in tanks for subsequent analysis in a laboratory at the surface.

Alternatively, for some properties, samples can be analyzed downhole in real time. The present invention relates both to monitoring sample clean up and to performing downhole analysis of samples at reservoir conditions of temperature and pressure. A downhole environment is a difficult one in which to operate a sensor. Measuring instruments in the downhole environment must operate under extreme conditions and limited space within a tool's pressure housing, including elevated temperatures, extreme vibration, and shock.

SUMMARY OF THE INVENTION

In one aspect of the invention a method is provided for estimating a property of a fluid downhole. Here, reflection (or reflecting) is meant to encompass reflection, diffraction, and interference of light. The method provides for exposing the fluid to light, reflecting light that has interacted with the fluid off of a micro electromechanical system (MEMS) tunable optical grating (TOG) having a first mirrored member and a second mirrored member. The method further provides measuring the light reflected from the TOG and estimating a property of the formation fluid from the measured light. For higher overall wavelength resolution, light that has interacted with the fluid can first be filtered using an optical bandpass filter or other means to select only those wavelengths in a narrow range of wavelengths before projecting that pre-filtered light onto the tunable grating.

In another aspect of the invention the method provides for varying a distance between the first mirrored member and the second mirrored member to sweep a wavelength of light reflected by the TOG over a range of wavelengths. In another aspect of the invention the method provides for exposing a second system to light. The second system further provides a second TOG having a third mirrored member and a fourth mirrored member, wherein the third mirrored member and the fourth mirrored member are substantially parallel to each other and not directly in contact with one another. The second system further provides a secondary formation fluid, estimating a property of the secondary formation fluid, comparing the property of the formation fluid to the property of the secondary formation fluid, and determining whether the formation fluid derives from the same formation compartment as the secondary formation fluid.

In another aspect of the invention the method provides for modulating the distance between the mirrored members by controlling a piezoelectric element. In another aspect of the invention modulating the distance between the mirrored members by controlling a micro-electromechanical device.

In another aspect of the invention the range of wavelengths includes but is not limited to a hydrocarbon band of wavelengths. The method further provides locating at least one peak in the range of wavelengths and performing wavelength modulation spectroscopy around a center wavelength for the at least one peak.

In another aspect of the invention the method of uses the measured light and a soft modeling technique to estimate the property of the formation fluid. In another aspect of the invention the method provides for estimating at least one of the set consisting of a carbon number distribution and percentage of drilling mud contamination.

In another aspect of the invention a downhole tool is provided for estimating a property of a fluid downhole that provides a light source that illuminates the fluid downhole, a TOG having two separated mirrored members that reflect a wavelength of light based on a control input, a photodetector that measures light that has interacted with the fluid downhole and been reflected by the TOG, and a processor in data communication with the photodetector that estimates a property of the fluid downhole from the data from the photodetector.

In another aspect of the invention the downhole further provides a circuit that adjusts the TOG for a wavelength of light and includes a modulator that modulates the wavelength. In another aspect of the invention a control input varies a distance between the two parallel members. In another aspect of the invention the optical filter further provides a piezoelectric element or a micro-electromechanical device that adjusts the distance between the two parallel members. In another aspect of the invention the processor uses the data from the photodetector and a soft modeling technique to estimate the property of the initial formation fluid.

In another aspect of the invention the downhole further provides a secondary formation fluid in optical communication with the light source and the TOG, wherein the processor estimates the property of the formation fluid based on a comparison to the secondary formation fluid.

Examples of certain features of the invention have been summarized here rather broadly in order that the detailed description thereof that follows may be better understood and in order that the contributions they represent to the art may be appreciated. There are, of course, additional features of the invention that will be described hereinafter.

BRIEF DESCRIPTION OF THE FIGURES

For a detailed understanding of the present invention, references should be made to the following detailed description of the exemplary embodiment, taken in conjunction with the accompanying drawings, in which like elements have been given like numerals, wherein.

DETAILED DESCRIPTION OF THE INVENTION

Figure 1:
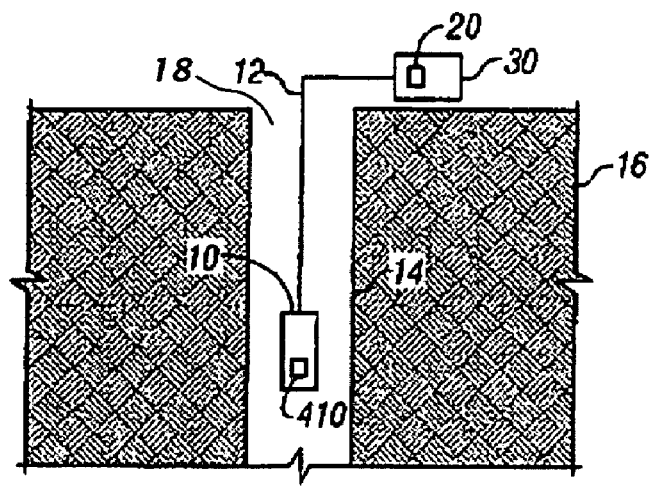
FIG. 1 is a schematic diagram of an illustrative embodiment of the present invention deployed on a wireline in a downhole environment.

Previously, commercial downhole optical spectrometers could be described as near-infrared filter photometers. That is, commercial downhole optical spectrometers have used fairly broadband individual optical filters that were centered at a handful of different discrete wavelengths. The bandwidth of each optical filter was typically 20-30 nm although a few filters may have provided a narrower bandwidth of only 11 nm, which is near the limit for interference filters that can be manufactured for downhole applications using today's technology. Also, there was often a substantial gap in wavelength coverage between the wavelength region covered by one optical filter and the wavelength region covered by the next optical filter so one did not obtain continuous spectra at nanometer resolution.

The present invention provides a tunable optical grating (TOG) for estimating a property of a fluid downhole. The TOG can be selected from electronically tunable optical Micro Electromechanical System (MEMS) gratings to collect spectra of downhole fluids with wavelength resolution on the order of a nanometer. The nanometer-resolution spectra can be used to, but not limited to, estimate or determine physical properties and composition (synthetic chromatogram), oil-based mud filtrate contamination, $H_2S$, and $CO_2$ concentrations for downhole fluids. The TOG reflects light at a wavelength selected by changing the spacing between mirrored members in the TOG. In an illustrative embodiment, the tunable wavelength range of TOG is continuous.

The TOG provides high wavelength resolution on the order of 1-2 nm downhole, thereby providing continuous nanometer-resolution spectroscopy (NRS) downhole. Most, if not all, of the currently available MEMS TOGs are not are rated by their manufacturer for the high temperatures (up to 175° C. or more) encountered downhole. Thus, the present invention provides, when desired, sorption cooling or another type cooling system to overcome temperature limitations to enable operation of the TOG at downhole temperatures up to and exceeding 175° C.

There are numerous advantages to using continuously TOGs. One advantage is that the present invention uses only a single photodetector to perform continuous NRS downhole. Using a single photodetector to collect data for all wavelengths greatly improves the quality of the spectra obtained because it eliminates the need to calibrate and normalize the spectral response and sensitivity between members of an array of photodetectors. A single detector also offers many practical design advantages. With a non-tunable grating the reflected light spectrum is spread out over some angle. If the angle between the grating and the detector is fixed, then an array of detectors such as a photodiode or CCD array is needed to collect the reflected light spectrum. Presently, there are no multiplexers for low level signals that can operate at the high-temperatures encountered downhole, so each photodiode in such an array would need to have its own amplifier circuit. Then, to measure light at a series of a hundred different wavelength steps would require a hundred photodiodes and a hundred amplifier circuits. All of these problems are eliminated by using a tunable grating with a single detector.

The present invention provides continuous NRS for estimating concentration of one gas in a mixture of gases such as a concentration of $H_2S$ in a natural gas mixture. The term continuous as used herein means that there are no gaps in wavelength coverage of the reflected light spectrum. That is, the difference in center wavelengths between any two neighboring wavelength channels does not exceed twice the full-width at half maximum wavelength response for either channel. The present example of the invention provides a single photodetector, rather than trying to synchronize or calibrate the response of two photo detectors at downhole conditions. Furthermore, because the present invention can rapidly and continuously change the wavelength of light reflected by the TOG, the present invention can also perform wavelength modulation spectroscopy (WMS) about a center wavelength (or frequency) of light. WMS is discussed in a number of papers and texts. In one embodiment of the invention, a hydrocarbon band (1650 nm -1850 nm) is continuously scanned and spectral peaks or other spectral features located within the band. WMS is then performed for each peak located in the band.

The present invention provides WMS, to obtain the first derivative of an absorption spectrum about one or more center wavelengths by modulating the TOG's wavelength about a selected center wavelength. To calculate the change in absorbance for a fluid sample (rather than absorbance, itself) using WMS, it is not necessary to determine how much transmitted light entered a sample but only how much the transmitted light changed from its average value after passing through the sample. WMS can also be performed to determine reflectance. Thus, by applying WMS, the present invention collects spectra using a "single beam" instrument with as much or better accuracy than a "dual beam" instrument for which errors can be introduced by differences between the two photodetectors (reference and sample) that are commonly used in dual beam instruments. WMS is performed by modulating the distance between two mirrored members in the TOG.

By definition, the absorbance A at wavelength $$\lambda \text{ is } A(\lambda) = \log_{10}[I_0(\lambda)/I(\lambda)] \tag{1}$$

where $I_0$ is the intensity of light entering the sample and I is the intensity of light exiting the sample. If one modulates the wavelength of light from $\lambda_1$ to some nearby wavelength, $\lambda_2$, then the change in absorbance, $\Delta A$, is given by, $$\Delta A = A(\lambda_2) - A(\lambda_1) = \log_{10}[I_0(\lambda_2)/I(\lambda_2)] - \log_{10}[I_0(\lambda_1)/I(\lambda_1)] \tag{2}$$

$$\Delta A = \log_{10}[I_0(\lambda_2)/I_0(\lambda_1)] - \log_{10}[I(\lambda_2)/I(\lambda_1)] \tag{3}$$

One defines, $$\Delta I = I(\lambda_2) - I(\lambda_1) \tag{4}$$

By modulating over a spectral region where the sample's absorbance is changing rapidly with wavelength (near an absorbance peak), one can assume that the fractional change in incident (source) intensity with wavelength is small compared to the fractional change in transmitted intensity with wavelength. That is, we assume that $I_0(\lambda_2)/I_0(\lambda_1)=1$ so that the first logarithmic term of (3) vanishes. Then, substituting (4) into the remaining term of (3) to obtain, $$\Delta A = -\log_{10}[(I(\lambda_1) + \Delta I)/I(\lambda_1)] = -\log_{10}[1 + \Delta I/I(\lambda_1)] \tag{5}$$

Note that $\Delta A$ now has no dependence on source intensity so it is not necessary to provide a second photodetector to obtain the source intensity nor an optical multiplexer to shuttle between source and transmitted light impinging on a single detector. This eliminates the need for a second detector (which can be difficult to precisely calibrate against the first detector, especially at extreme downhole temperatures) and reduces or eliminates the need for a multiplexer to switch between the two intensities.

Because $\Delta\lambda = \lambda_2 - \lambda_1$, is very small, it can be assumed that $\Delta I << I(\lambda_1)$. Then, defining $\epsilon$, $$\epsilon = \Delta I / I(\lambda_1). \tag{6}$$

Note that $\Delta I$ can be considered as an "AC" signal which is modulated by modulating $\lambda_2$ about a fixed $\lambda_1$. Similarly, $I(\lambda_1)$ can be considered as a "DC" signal at a fixed $\lambda_1$. The ratio, $\epsilon$, of "AC" to "DC" is used to calculate $\Delta A$. In this way, absorbance spectroscopy can be performed without having to determine baseline light transmission through an empty sample cell.

Then, one can employ the expansion for the natural logarithm about unity, $$\ln(1+\epsilon) = \epsilon - \epsilon^2/2 + \epsilon^3/3 - \epsilon^4/4 \ldots \text{ for } -1 < \epsilon < 1 \tag{7}$$

and the identity, $\log_a(N)/\log_b(a)$ to write, $$\Delta A = -[\epsilon - \epsilon^2/2 + \epsilon^3/3 - \epsilon^4/4 - + \ldots]/2.303 \tag{8}$$

Finally, one estimates the first derivative of spectrum about $\lambda_1$ as $$\Delta A/\Delta\lambda = -[\epsilon - \epsilon^2/+\epsilon^3/-\epsilon^4/4 + \ldots]/(2.303\Delta\lambda) \tag{9}$$

The present invention provides a nanometer-resolution spectrometer using a TOG to enable nanometer-resolution spectral measurements to determine or estimate physical and chemical properties of a gas or fluid, including the percent of oil-based mud filtrate contamination in crude oil samples. The present invention also enables spectral measurements to determine or estimate the mole fraction or percent of chemical groups (aromatics, olefins, saturates) in a fluid such as a crude oil or gas sample. The present invention also enables analysis of nanometer-resolution spectral measurements to determine or estimate or directly measure gas oil ratio (GOR) for a fluid.

The illustrative embodiment provides a nanometer-resolution spectrometer incorporating a TOG to enable nanometer-resolution spectral measurement to determine or estimate the composition of a fluid. The illustrative embodiment can determine or estimate other parameters of interest of a fluid, such as to estimate whether crude oil contains wet gas (high methane) or dry gas (low methane), which is determined by the relative concentrations of $C_1$, $C_2$, $C_3$, $C_4$. The illustrative embodiment provides a nanometer-resolution spectrometer using a TOG to enable nanometer-resolution spectral measurements to determine or estimate $CO_2$ in methane gas or $CO_2$ dissolved in a fluid, for example, crude oil.

The illustrative embodiment provides a nanometer-resolution spectrometer using a TOG to enable nanometer-resolution spectral measurement to provide improved correlation of spectral measurements to physical properties (API Gravity, cloud point, bubble point, asphaltene precipitation pressure, etc.) or chemical properties (acid number, nickel, vanadium, sulfur, mercury, etc.) of crude oil. The illustrative embodiment provides a nanometer-resolution spectrometer using a TOG to provide nanometer-resolution spectral measurement to determine or estimate fluid properties, for example, the phytane/pristane ratios of crude oil.

The illustrative embodiment provides a nanometer-resolution spectrometer using a TOG to enable nanometer-resolution spectral measurement to determine or estimate the fluid properties such as the amount of $H_2S$ that is dissolved in crude oil, which is commercially important because the value of a barrel of crude oil drops with increasing $H_2S$ concentration due to extra costs of handling and removal of the $H_2S$.

The illustrative embodiment provides a nanometer-resolution TOG for spectral measurements from which a correlative equation derived from soft modeling (chemometrics such as multiple linear regression, principal components regression, partial least squares, or a neural network) can be used to infer physical and chemical properties of sample formation fluids or other fluids. The illustrative embodiment takes advantage of the TOG's rapid and continuous wavelength switching capability to perform derivative spectroscopy or WMS to find spectral peaks on a shoulder of another larger spectral peak or to greatly improve signal to noise ratios and makes it possible to observe subtle changes.

The illustrative embodiment enables quantification of aromatics, olefins (unlikely in crude oil but common in OBM filtrate so it can be used to quantify the percentage of filtrate), saturates, methane, ethane, propane, and butane. The illustrative embodiment determines or estimates the percentage of oil based mud filtrate contamination downhole, particularly if the base oil is aromatic-free (unlike crude oil) but olefin-rich (also unlike crude oil).

In another embodiment, by changing the wavelength (or frequency) of light reflected by the TOG by tuning the TOG, the present invention also performs Raman spectroscopy in combination with a single wavelength detector for the light that is Raman scattered by the sample.

One difficulty with implementing a TOG spectrometer downhole is temperature. Typically, manufacturers rate tunable optical filters to temperatures of 80° C. or less. The illustrative embodiment of the invention combines a TOG with a downhole sorption cooling system, when desired. The sorption cooling system cools the TOG spectrometer to assist operating the TOG spectrometer at high ambient temperatures downhole. The TOG and associated TOG spectrometer components can be placed in thermal contact with a source of water (either as a liquid or as a hydrate). The TOG is cooled as water is evaporated from liquid or released by hydrate. The resulting water vapor which carries heat away from the TOG and is sorbed by a sorbent, which becomes hotter in the process. The sorbent transfers its excess heat to the well bore fluid with which it is in thermal contact. It would also be useful to determine the change in response of the TOG with temperature so that one could correct for its temperature response if the TOG's temperature changed substantially during the downhole job as might occur if one ran out of water coolant before the job was completed.

In an illustrative embodiment, a TOG is used to perform nanometer-resolution spectroscopy sweeps of the section of the hydrocarbon band which spans from about 1650-1850 nm. Other wavelength bands can be swept as well depending on what elements or measurements are desired in measuring spectral transmissivity, reflectivity, absorbance or fluorescence luminance response. From these TOG transmissivity, reflectivity, fluorescence luminance or absorbance spectral measurements, the present invention quantifies aromatics, olefins (unlikely in crude oil but common in OBM filtrate, which therefore provides one way to estimate filtrate contamination percentage based on olefin measurements), saturates, methane and possibly ethane, propane, and butane. With TOG nanometer-resolution spectroscopy, the illustrative embodiment determines or estimates the percentage of oil based mud (OBM) filtrate contamination downhole in a formation fluid sample, particularly if the OBM contaminants are aromatic-free but olefin-rich. The illustrative embodiment can estimate the degree of formation fluid clean up or removal of contamination by monitoring a property of OBM present in a formation fluid.

Furthermore, with nanometer-resolution spectroscopy provided by the present invention, the illustrative embodiment can determine or estimate subtle chemical composition differences between two formation fluids taken at different depths in a well bore. Such differences can be used to assess the compartmentalization of a reservoir, which means to determine whether different sections of a reservoir are separate compartments (across which fluids do not flow) or whether they are connected to each other. Separate compartments must be drained separately (separate wells) and may need different types of processing for their fluids.

Multi-billion dollar decisions on how to develop a reservoir (well locations, types of production facilities, etc.) are based on whether or not a reservoir is compartmentalized. One way to assess compartmentalization is based on phytane/pristane ratios of liquid crude oil or by using any other distinguishing features such as any unexpected subtle differences in the fluid spectra that are capable of being resolved using a TOG. Gravity segregation will cause some expected spectral differences in fluids from different depths even when there is no compartmentalization. For example, one expects the top of a column of crude oil to be more gas rich than the bottom. For a 2 mm path length, the dominant liquid (C6+) hydrocarbon optical absorption peaks are near 1725 nm, while the corresponding absorbance peaks of hydrocarbon gases such as methane, ethane, propane, butane, lie between 1677 nm and 1725 nm. Subtle differences in spectra outside the regions where these hydrocarbon gases absorb are unexpected and therefore provide evidence of compartmentalization.

In one aspect of the invention, MEMS or piezoelectric devices are disposed in between a first and second mirrored member for operatively applying forces to vary a distance between the first and second mirrored members. MEMS and piezoelectric technology are well known to those skilled in the art. MEMS is a process whereby micron-sized mechanical devices are fabricated on silicon wafers by photolithography and etching techniques. These mechanical devices are formed on integrated circuit chips so that devices, which incorporate MEMS technology, essentially become miniature electromechanical systems. MEMS devices are activated by analog voltages which create an electric field that will cause the MEMS devices to physically deflect since they are made of silicon and therefore respond to the electric field.

Accordingly, a DC power supply controlled by a processor is connected to MEMS or piezoelectric devices through leads to bias MEMS devices and variation in the distance between the first and second mirrored members. One of the advantages of using MEMS devices on a silicon integrated circuit chip is that MEMS devices are low mass, low power, and low voltage devices. The low mass means that the MEMS device has low sensitivity to shock and vibration, which is important in wireline applications and even more important in logging while drilling applications, where shock and vibration is even worse. The low voltage and low power means that one can use ordinary printed circuit board designs and use battery power in conjunction with the MEMS devices if desired. Preferably, voltages of between about 0 and 10 volts are provided to control the desired deflection of MEMS or piezoelectric devices. These low voltages help to ensure low attenuation of the cavity signals and low insertion losses. Applied voltages of between about 0 and 10 volts also reduce the polarization dependent loss for high signal attenuation. Moreover, while power supply source has been described as a DC power supply, it will be recognized by those with skill in the art that power supply could alternately be an AC source with appropriate rectifying circuitry, or an AC source that directly applies power to MEMS devices where MEMS devices are configured for actuation by AC power.

MEMS devices can be any kind of micro electro mechanical system actuator operable to uniformly and easily move mirrored members of a tunable optical grating. For example, cantilevered arms, pivot points, spring-like or other resilient mechanisms, levers, moment arms, torque generating devices, and other devices and equivalents thereof that can apply the correct amount of force to the mirrored members are all configurable in silicon MEMS devices and are within the scope of the present invention. In the illustrative embodiment, MEMS devices are implemented by a pair of pistons that are extendable to uniformly push against mirrored mirrors to separate mirrored members. The MEMS device is physically connected to leads to receive power from the power supply.

The illustrative embodiment provides a downhole instrument that can measure real-time, nanometer-resolution, continuous optical spectra of fluids, particularly over the hydrocarbon band region of the spectrum. Nanometer-resolution spectra (that is, resolution in the 1-2 nanometer range) over the near-infrared hydrocarbon band (1650-1850 nm) contain detailed information about hydrocarbons. Such information is of high commercial value to the oil industry. For example, from the hydrocarbon band region, one can obtain information about the ratio of methyl (—$CH_3$) to methylene (—$CH_2$), which is indicative of the average hydrocarbon chain length and information on the relative concentrations of methane, ethane, propane, butane, and so on.

This spectral region also contains information on the concentrations of aromatics, olefins, and paraffins, which could be used for quantifying the percentage of oil-based mud (OBM) filtrate in a crude oil mixture. For example, for environmental friendliness, synthetic base oils for OBMs are designed to be free of aromatics, whereas crude oils always have some aromatics. Conversely, many synthetic muds contain olefins or esters, which are not present in crude oils. These distinctions provide a means to quantify percentages of OBM filtrate in mixtures of filtrate with crude oil. Of course, to reliably glean such subtle information from the spectra one should have high spectral resolution (both in wavelength and absorbance) as provided in an illustrative of the present invention.

One can assess hydrocarbon chain length from the ratio methyl to methylene by applying Fourier transform infrared (FTIR) spectroscopy to individual fluid inclusions greater than 15 microns in rock using an A-590 Bruker microscope linked to an FTIR Bruker IFS 88 spectrometer (J M Dereppe, J. Pironon, C. Moreaux, *American Mineralogist*, v. 79, p. 712-718, 1994). An infrared beam, and an MCT detector, cooled with liquid N2, allowed the IR detection between 600 and 5000 cm−1 (Barres et al., 1987). The spectra, presented in absorbance units and wave numbers (cm−1), were recorded in the transmission mode with a spectral resolution of 4 cm−1 after 400 accumulations. A chain-length coefficient can be calculated by comparing CH3-CH2 ratio of the sample to the same ratios measured on a standard n-alkane series.

In an illustrative embodiment, the present invention provides a TOG to reflect a wavelength of broad band or white light. White light that has interacted with a fluid sample is reflected off of the TOG to a sensor. The sensor can include, but is not limited to a single photodetector and amplifier which can sense the light reflected off of the TOG. A continuously variable wavelength control is provided to the TOG to enable creation of nanometer-resolution spectra for performing chemometric correlations for estimation of percentage of oil based mud filtrate to gas oil ratio and spectrally-inferred synthetic chromatograms.

In an illustrative embodiment white light is transmitted through a first window, though a formation fluid or down hole fluid, through a second window and onto the TOG. The TOG acts as a diffraction element. Light is detected as it is reflected off of the TOG. Control system electronics continuously adjust the voltages applied to various sections of the TOG to change the wavelength or wavelengths of light reflected by the TOG within the selection wavelength range. A photodetector is used to detect the light reflected off of the TOG. When necessary, a transform, such as a Hadamard transform can be used to recover a spectrum for the reflected light.

Spectral peaks can be identified in the reflected light collected from the swept wavelength band. The TOG can oscillate around a single wavelength coincident with a center wavelength for one or each of the spectral peaks for derivative spectroscopy. Derivative spectroscopy reduces the effects of baseline offset and artifacts. Reduction of offsets and artifacts facilitates maintenance of robust chemometric predictions of fluid properties based on spectra for the fluid.

The illustrative embodiment provides a piezoelectric or MEMS controlled TOG that is suitable for downhole use in part because the TOG is small, light weight and temperature resistant. In an illustrative embodiment, the TOG is resistant to vibration and shock downhole because it can be a low mass device manufactured on an electronic semiconductor device or piezoelectric material. In an illustrative embodiment, the TOG is also physically small so that it can be easily retrofitted into an existing downhole tool with minimal reengineering for physical space, power, light or control. In an illustrative embodiment, the TOG can potentially withstand temperatures up to 175° C. or more, which makes it suitable to withstand high temperatures for downhole use. In an illustrative embodiment, sorption can be added to bolster the TOG's ability to withstand downhole temperatures.

In an illustrative embodiment, the TOG also has no macroscopically moving parts. The wavelength of light reflected by the TOG is controlled by microscopic movement varying a distance between two mirrored members. Thus in an illustrative embodiment, the TOG is durable and robust, thus suitable for downhole use.

In another embodiment, white light is alternately directed through an unknown fluid sample and a reference chamber containing a reference compound having a known optical spectrum. Spectra are collected for the unknown fluid and for the reference fluid. The spectrum of the reference fluid is compared and correlated to the spectrum of the unknown fluid sample. Thus, through comparing and correlating the unknown fluid spectrum with the reference fluid spectrum over wavelength regions where the unknown fluid's matrix spectrum does not interfere with the reference compound's spectrum, the concentration of reference compound in the unknown fluid matrix can be estimated. For example, if the reference fluid contains one hundred parts per million (PPM) of a particular component (for example, $H_2S$) and the unknown fluid has a spectrum which looks the same but which has twice the absorbance at each non-interfering wavelength, then the unknown fluid can be estimated to contain two hundred PPM $H_2S$.

Turning now to FIG. 1, FIG. 1 is a schematic diagram of an illustrative embodiment of the present invention deployed in a borehole 18 on a wire line in a downhole environment. As shown in FIG. 1, a downhole tool 10 containing a downhole MEMS nanometer-resolution spectrometer 410 is deployed in a borehole 14. The borehole 18 is formed in formation 16. Tool 10 is deployed via a wireline 12. Data from the tool 10 can be transmitted to the surface to a computer processor 20 with memory inside of an intelligent completion system 30.

Figure 2:
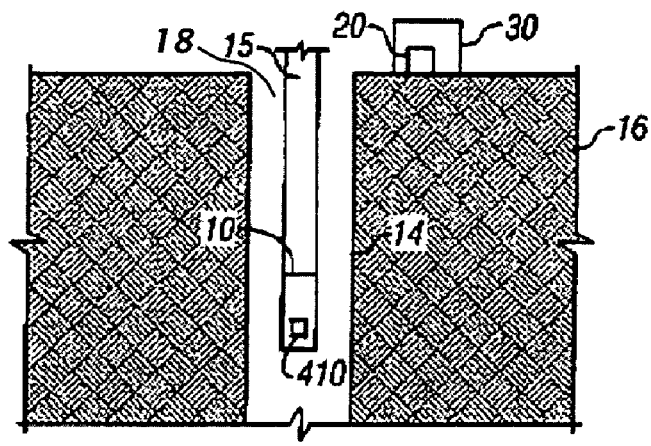
FIG. 2 is a schematic diagram of an illustrative embodiment of the present invention deployed on a drill string in a monitoring while drilling environment.
Figure 3:
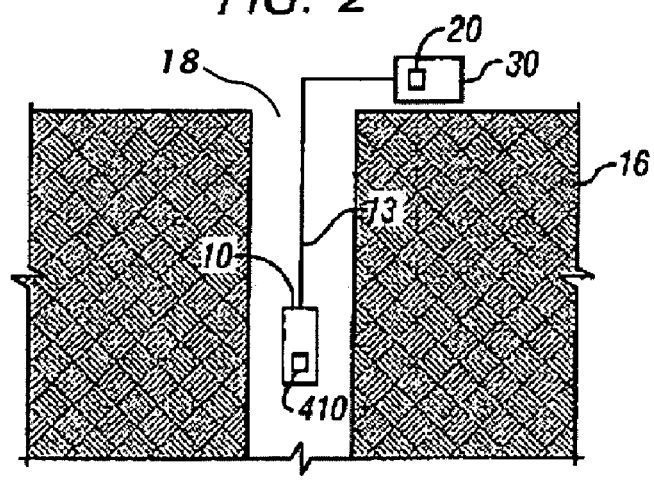
FIG. 3 is a schematic diagram of an illustrative embodiment of the present invention deployed on a flexible tubing in a downhole environment.

FIG. 2 is a schematic diagram of another illustrative embodiment having a MEMS nanometer-resolution spectrometer deployed on a drill string 15 in a monitoring while drilling environment. FIG. 3 is a schematic diagram of another illustrative embodiment having a MEMS nanometer-resolution spectrometer deployed on a flexible tubing 13 in a downhole environment. Sampling and analysis by MEMS nanometer resolution spectrometer 410 can be performed at variable depths whether deployed from a wire line 12, drill string 15, or flexible tubing 13.

Figure 4:
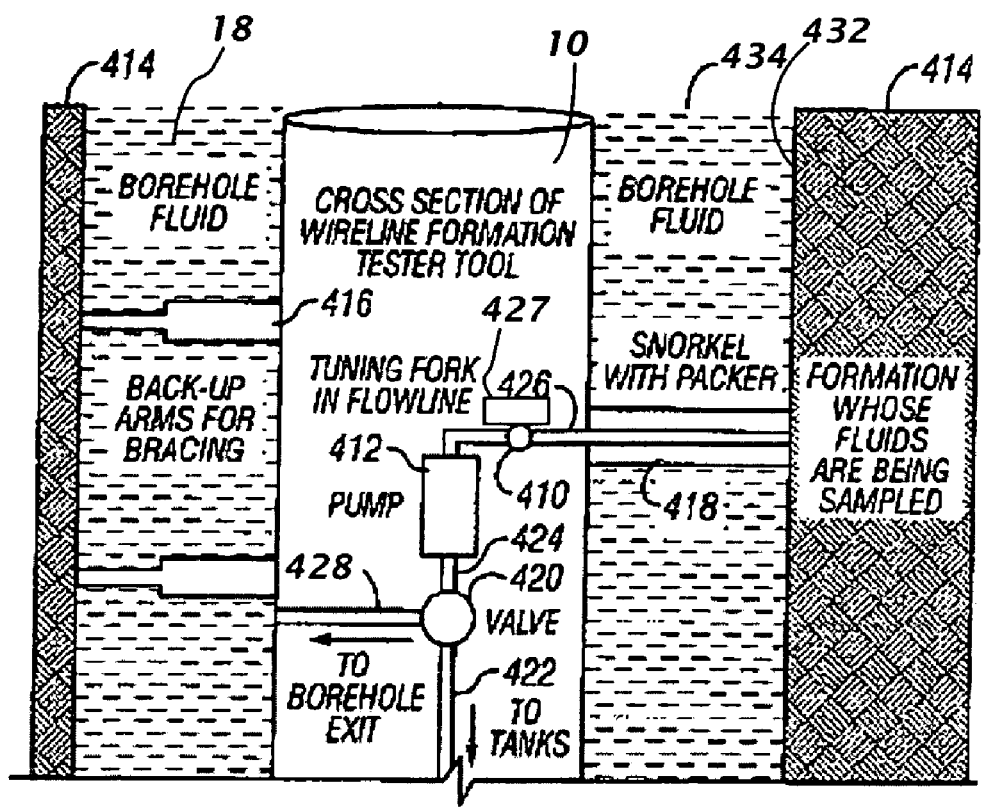
FIG. 4 is a schematic diagram of an illustrative embodiment of the present invention as deployed in a wireline downhole environment showing a cross section of a formation tester tool.
Figure 5:
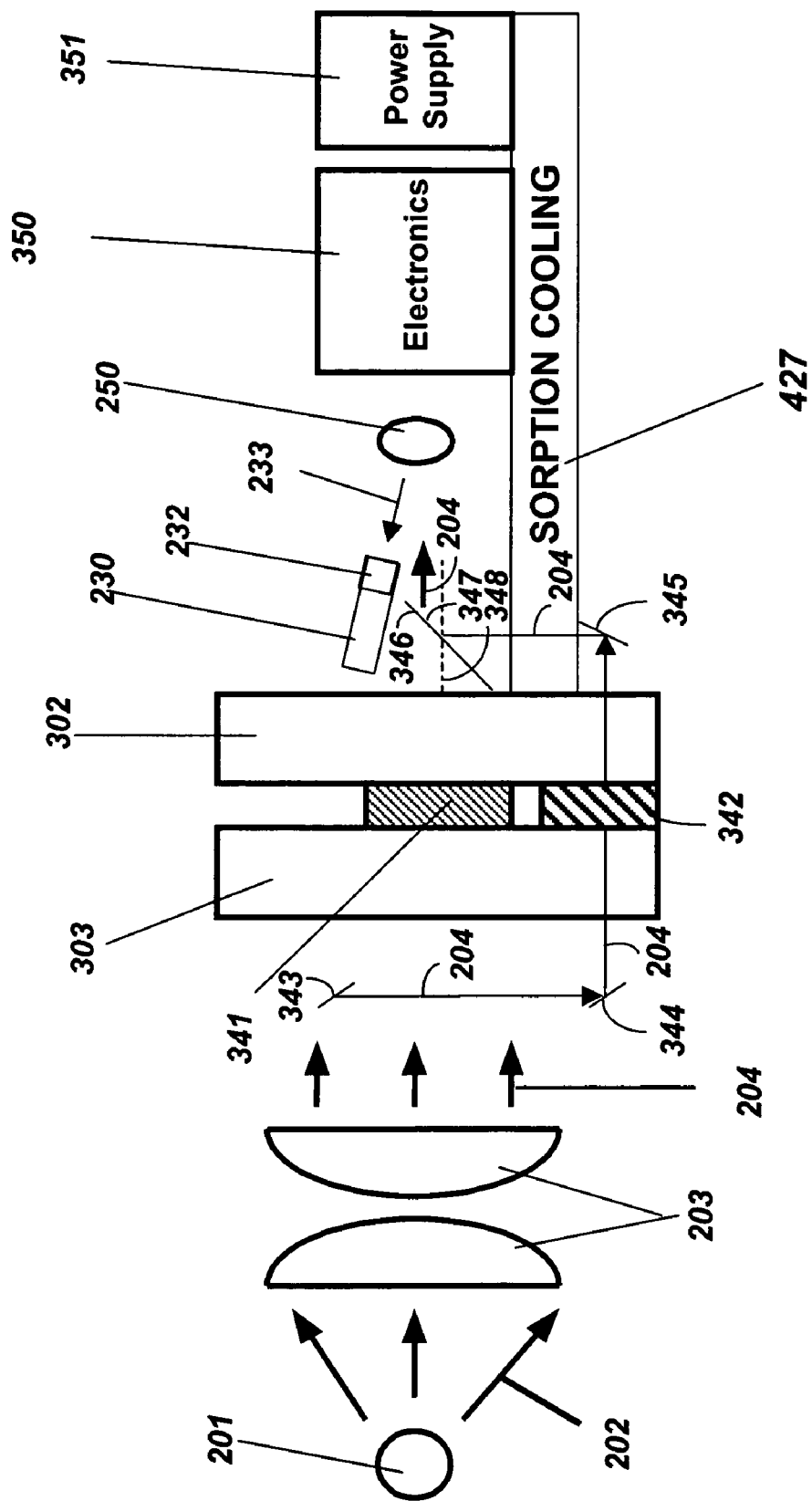
FIG. 5 is a schematic diagram of an illustrative embodiment showing a micro electromechanical system (MEMS) tunable optical grating (TOG) spectrometer.
Figure 6:
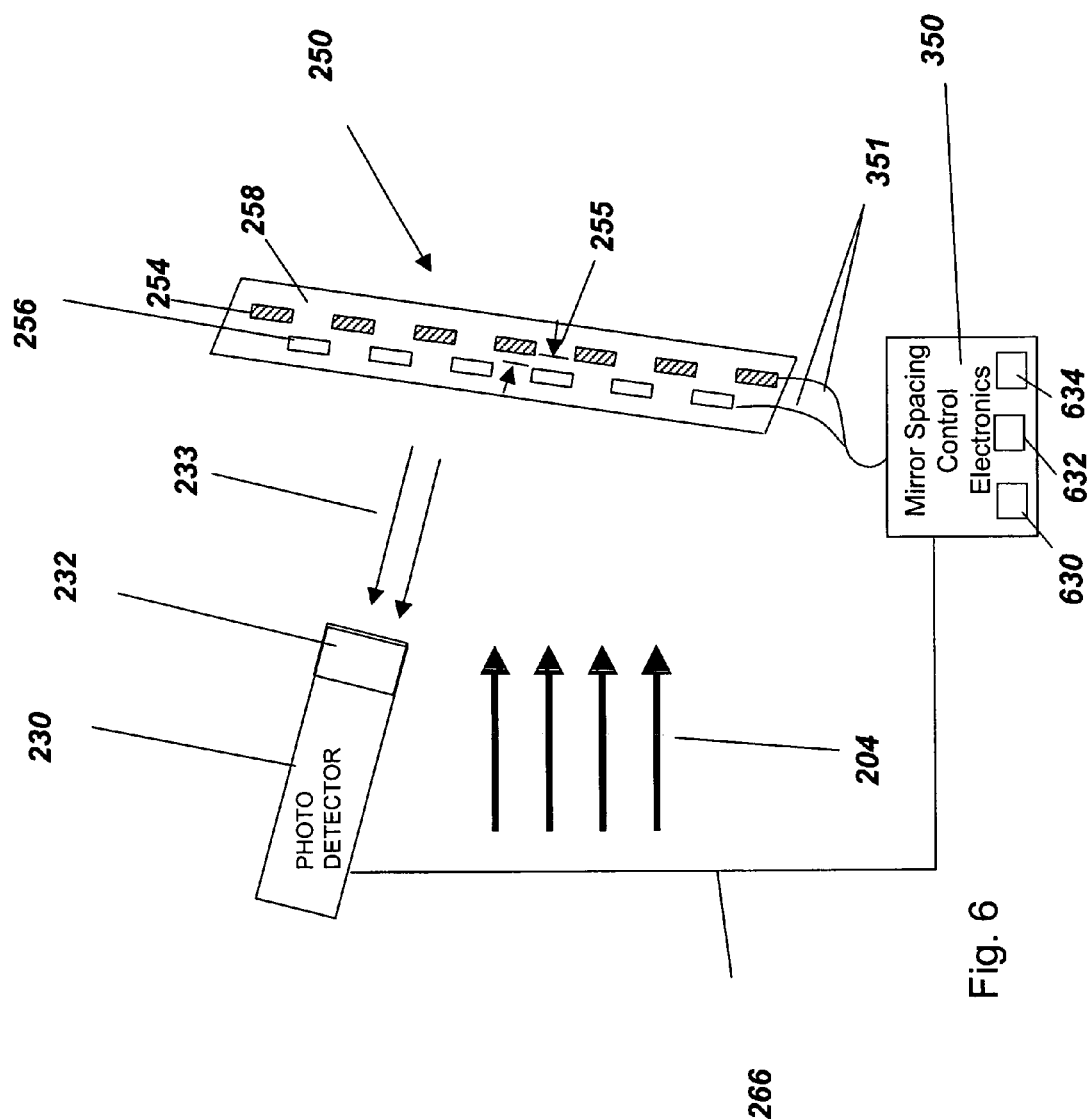
FIG. 6 is a schematic diagram of mirrored members in a TOG in an illustrative embodiment.

FIG. 4 is a schematic diagram of an illustrative embodiment of the present invention as deployed in a borehole 18 in a wire line downhole environment showing a cross section of a wireline formation tester tool 10. As shown in FIG. 4, the tool 10 is deployed in a borehole 14 filled with borehole fluid 434. The tool 10 is positioned in the borehole 18 by backup support arms 416. A snorkel 418 with packer contacts the borehole wall 432 for extracting formation fluid from the formation 414. In an illustrative embodiment, tool 10 contains downhole MEMS nanometer-resolution spectrometer 410 containing the TOG disposed in or near flow line 426. The control and acquisition electronics (350 as shown in FIG. 5) which include processor, memory and data bases shown in FIG. 6 are housed in the tool 10. Pump 412 pumps formation fluid from formation 414 into flow line 426. In the illustrative embodiment formation fluid travels through flow line 426 and into valve 420 which directs the formation fluid to line 422 to save the fluid in a sample tank or to line 428 where the formation fluid exits to the borehole.

Turning now to FIG. 5, an illustrative embodiment of the invention is shown. As shown in FIG. 5, a light source 201 provides light 202 to collimating lens 203. Collimated white light 204 is transmitted through a first window 303, though a formation fluid or down hole fluid 341, through a second window 302 and onto the TOG 250. The tunable grating acts as a diffraction element. Reflected light 233 is detected by optical detector 230 as it is reflected off of the TOG 250. Mirror spacing control electronics 350 sweep the wavelength of the TOG 250 over a selected band of frequencies and wavelengths. A photodetector 230 and an order-sorting blocking filter 232 are used to detect the light reflected off of the TOG 250. A transform, for example, a Hadamard type transform can be used to recover a spectrum or spectra for the fluid from the detected light. Electrical power is provided by power supply 351.

To collect a spectrum more quickly, the entire MEMS tunable optical grating, consisting of a multiplicity of mirrored members, can be subdivided into a hundred or more regions or sets of mirrored members, each of which is then operated as if it was a separate grating dedicated to a single wavelength. Then, each separate grating set can either project or not project its dedicated wavelength of light onto the spectrometer's photodetector. Each separate grating can then be thought of as an "on-off" filter for its dedicated wavelength. This configuration allows one to project more than one wavelength (e.g. 50 wavelengths) simultaneously onto the photodetector and then sequentially cycle through various predetermined patterns of projected wavelengths. A mathematical (Hadamard) transform can then be used to process the data of photodetector response for each pattern to determine the amount of light that would have detected at each individual wavelength. This approach is the basis of Hadamard spectroscopy. This configuration also allows one to mimic absorption spectra of a reference sample (e.g. H2S) by projecting all wavelengths but those wavelengths at which the sample would absorb light.

In an alternative embodiment, a set of light diverters, for example, mirrors 343, 344, 345, and 347, can be used to redirect light 204 through reference sample 342. Light diverter 347 can be rotated so that in the position shown, mirror 347 reflects light 204 from light diverter 345 and intercepts light from sample 341. Light 204 reflects off of mirror 343 to mirror 344 through reference sample 342 to mirror 345 where it is reflected off of mirror 347 into light path 204 to impinge on TOG 250.

The back side 346 of mirror 347 intercepts light passing through sample 341 when in the position shown in FIG. 5 and reflects light passing through the reference sample. When mirror 347 is rotated from the position shown to the position shown by dashed line 348, light from the sample 341 is not intercepted and passes to strike TOG 250 and light from reference sample 342 is not reflected to TOG 250.

Rotating mirror 347 is positionally controlled by a motor controlled by electronics 350. Thus, the illustrative embodiment enables comparison of spectra for reference sample 342 to spectra for reference sample 341.

Spectra for reference sample 342 can be obtained at the surface and compared to spectra for the reference sample obtained downhole to recalibrate the TOG spectrometer for downhole temperature measurements.

Turning now to FIG. 6, in the illustrative embodiment, the TOG 250 comprises a multiplicity of mirrored members 254 and 256, which may include a lower set of grating mirrors 254 and an upper set of grating mirrors 256 on a MEMS semiconductor chip 258. The mirrored members 254, 256 can be divided into smaller sets or regions, which can be independently controlled. A piezoelectric device may be incorporated into the MEMS chip. A feed back loop 266 may be provided between the optical detector 230 and mirror spacing control electronics 350. The mirror spacing control electronics 350 can include a processor 630, memory 632 and database 634 for storing a computer program for execution by the processor. The computer program can contain instructions to find peaks within a hydrocarbon band and perform derivative spectroscopy around a center wavelength for each of the peaks. The spacing 255 or distance between the upper 256 and lower 254 mirrored members determines the wavelength of light reflected off of the TOG 250 to the optical detector 230 through the order-sorting blocking filter 232.

Figure 7:
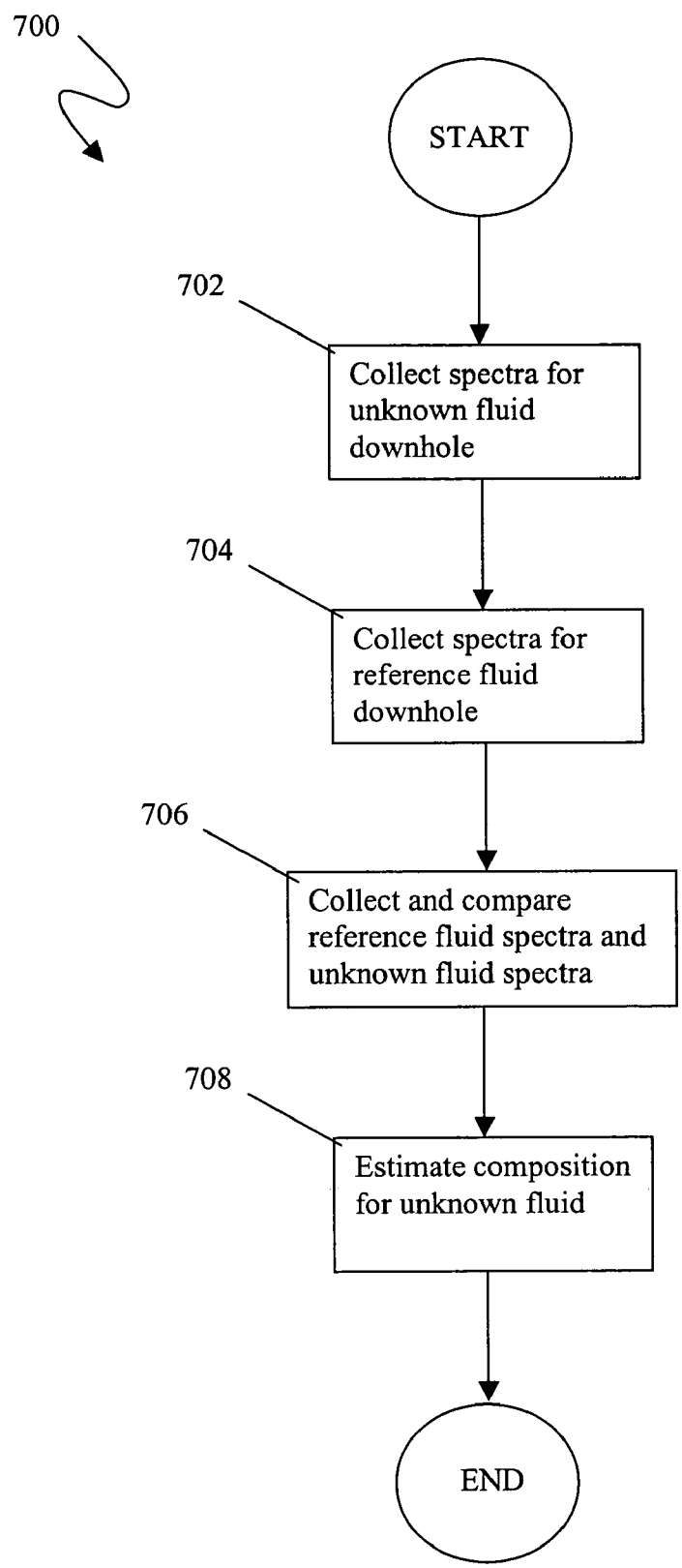
FIG. 7 is a flow chart illustrating collection and analysis of spectra for an unknown fluid in an illustrative embodiment.

Turning now to FIG. 7, a flow chart 700 is shown wherein an illustrative embodiment spectra is collected for unknown fluid downhole at block 702. Spectra is then collected for a reference fluid sample downhole at block 704. Reference fluid spectra and unknown fluid spectra are collected and compared at block 706. Composition for the unknown fluid sample is estimated at block 708 and the process ends.

Figure 8:
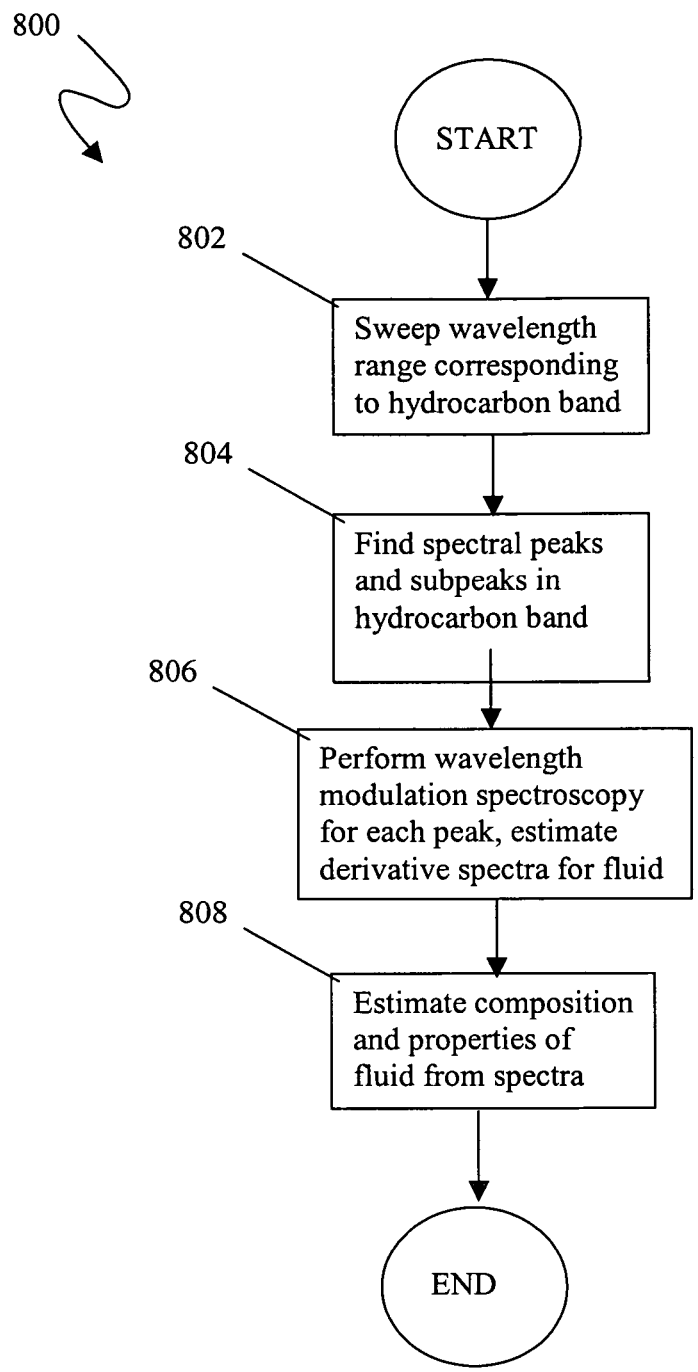
FIG. 8 is a flow chart illustrating sweeping a wavelength range to find spectral peaks in an illustrative embodiment.

Turning now to FIG. 8, a flow chart 800 is shown wherein in another illustrative embodiment a wavelength range is continuously (that is without an interruption in spectral coverage) swept over a hydrocarbon band at block 802 for an unknown fluid. In an illustrative embodiment the process finds spectral peaks and subpeaks (on the shoulders of larger peaks) in the hydrocarbon range at block 804. Wavelength modulation spectroscopy is performed for each peak and subpeak and derivative spectra estimated at block 806. Composition of the unknown fluid is estimated from spectra at block 808 and the process ends.

Spectral peaks can be identified in the hydrocarbon band of wavelengths swept by mirrored member spacing control and data acquisition electronics 350. Derivative spectrometry can be performed centered about a single wavelength coincident with a single center wavelength for one or each of the spectral peaks. Derivative spectroscopy reduces the effects of baseline offset and artifacts. Reduction of offsets and artifacts facilitates maintenance of robust chemometric predictions of fluid properties based on spectra for the fluid.

While the foregoing disclosure is directed to the exemplary embodiments of the invention various modifications will be apparent to those skilled in the art. It is intended that all variations within the scope of the appended claims be embraced by the foregoing disclosure. Examples of the more important features of the invention have been summarized rather broadly in order that the detailed description thereof that follows may be better understood, and in order that the contributions to the art may be appreciated.

What is claimed is:

1. A method for estimating a property of a fluid downhole, comprising:
    exposing the fluid to light downhole;
    reflecting the light off of a tunable optical grating (TOG);
    measuring the light reflected from the TOG;
    locating at least one peak in a range of wavelengths;
    performing wavelength modulation spectroscopy around a center wavelength for the at least one peak; and
    estimating a property of the fluid from the measured light.

2. The method of claim 1, further comprising:
    varying a distance between a first TOG mirrored member and a second TOG mirrored member to sweep a wavelength of light reflected by the TOG over the range of wavelengths.

3. The method of claim 1, further comprising:
    exposing a secondary fluid to light;
    estimating a property of the secondary fluid;
    comparing the property of the fluid to the property of the secondary fluid; and
    determining whether the fluid derives from the same formation compartment as the secondary fluid.

4. The method of claim 2, wherein modulating the distance comprises controlling at least one of the set consisting of a piezoelectric element and a micro-electromechanical device.

5. The method of claim 2, wherein the range of wavelengths comprises a hydrocarbon band of wavelengths.

6. The method of claim 1, wherein estimating further comprises using a soft modeling technique to process the measured light to estimate the property of the formation fluid.

7. The method of claim 1:
    wherein estimating further comprises estimating at least one of the set consisting of a carbon number distribution, percentage of drilling mud contamination, and gas-oil ratio (GOR).

8. The method of claim 1, wherein the light to which the fluid is exposed is light reflected off of the TOG.

9. The method of claim 1, wherein the light reflected off of the TOG is light that has interacted with the fluid.

10. The method of claim 1, further comprising:
dividing the TOG into a plurality of regions;
operating each of the plurality of regions at a separate wavelength; and
processing the light reflected from the TOG with a Hadamard transform.

11. The method of claim 10, further comprising:
operating each of the plurality of regions as a separate grating dedicated to a single wavelength.

12. A method for estimating a property of a fluid downhole, comprising:
exposing the fluid to light downhole;
reflecting light off of a tunable optical grating (TOG);
measuring the light reflected from the TOG;
exposing a reference fluid to light;
locating at least one peak in a range of wavelengths;
performing wavelength modulation spectroscopy around a center wavelength for the at least one peak;
reflecting the exposed light that has interacted with the reference fluid off of the TOG;
measuring light reflected off the TOG that has interacted with the reference fluid; and
estimating the property of the fluid from the measured light that has interacted with the fluid-in comparison with the measured light that has interacted with the reference fluid.

13. The method of claim 12, further comprising:
estimating a change in the property of the reference fluid to a property of the reference fluid obtained at a surface temperature; and
calibrating the estimate of the property of the fluid based on the change in the property of the reference fluid.

14. A downhole tool for estimating a property of a fluid, comprising:
a light source that illuminates the fluid downhole;
a photodetector in optical communication with the light that measures light from the fluid downhole;
a tunable optical grating (TOG) having a pluarality of mirrored members in optical communication between light source and the photodetector wherein the fluid is in optical communication between the light source and photodector;
a processor in data communication with the photodetector that estimates a property of the fluid; and
a computer program containing instructions executed by the processor, the computer program further comprising instructions to find at least one peak within a hydrocarbon band and instructions to perform derivative spectroscopy around a center wavelength for the peak.

15. The downhole tool of claim 14, further comprising:
a circuit that adjusts the TOG to vary a wavelength of light reflected by the TOG, the computer program further comprising instructions to compare the property of the fluid to the property of the secondary fluid and determine whether the fluid derives from the same formation compartment as the secondary fluid.

16. The downhole tool of claim 14, further comprising:
a filter positioned between the fluid and the TOG that reduces spectra of the light from the fluid.

17. The downhole tool of claim 14, further comprising a control input in electrical communication with the processor to vary distance between the plurality of mirrored members on the TOG.

18. The downhole tool of claim 17, wherein the TOG further comprises a piezoelectric element positioned between the plurality of mirrored members.

19. The downhole tool of claim 17, wherein the TOG further comprises a micro-electromechanical system positioned between the mirrored members.

20. The downhole tool of claim 14, wherein the processor is configured to use the data from the photodetector and a soft modeling technique to estimate the property of the fluid.

21. The downhole tool of claim 14, further comprising:
a reference fluid in optical communication with the light source and the TOG, wherein the processor is configured to estimate the property of the fluid based on a comparison to the reference fluid.

22. The downhole tool of claim 14, wherein the mirrored members further comprises a multiplicity of mirrored members divided into sets.

23. The downhole tool of claim 22, wherein the mirrored members are individually controllable.

24. The downhole tool of claim 22, wherein the processor is configured to divide the TOG into a plurality of regions, operate each of the plurality of regions at a separate wavelength and process the light reflected from the TOG with a Hadamard transform.

25. The downhole tool of claim 24, wherein the processor is further configured to operate each of the plurality of regions as a separate grating dedicated to a single wavelength.

* * * * *